US012685850B2

(12) United States Patent
Chen et al.

(10) Patent No.: US 12,685,850 B2
(45) Date of Patent: Jul. 21, 2026

(54) ATRIAL SHUNT DECOMPRESSION DEVICE, WEAVING DEVICE AND WEAVING METHOD THEREOF

(71) Applicant: WUHAN VICKOR MEDICAL TECHNOLOGY CO., LTD., Hubei (CN)

(72) Inventors: Song Chen, Wuhan (CN); Xueli Wang, Wuhan (CN); Changdong Zhang, Wuhan (CN); Ming Sun, Wuhan (CN); Tao Zhu, Wuhan (CN); Liang Mao, Wuhan (CN)

(73) Assignee: WUHAN VICKOR MEDICAL TECHNOLOGY CO., LTD., Wuhan (CN)

( * ) Notice: Subject to any disclaimer, the term of this patent is extended or adjusted under 35 U.S.C. 154(b) by 1035 days.

(21) Appl. No.: 17/790,122

(22) PCT Filed: Sep. 11, 2019

(86) PCT No.: PCT/CN2019/105369
§ 371 (c)(1),
(2) Date: Jun. 30, 2022

(87) PCT Pub. No.: WO2021/046753
PCT Pub. Date: Mar. 18, 2021

(65) Prior Publication Data
US 2023/0045035 A1 Feb. 9, 2023

(51) Int. Cl.
*D03D 1/00* (2006.01)
*A61B 17/00* (2006.01)
(Continued)

(52) U.S. Cl.
CPC ............. *A61M 27/002* (2013.01); *D03D 1/00* (2013.01); *D04C 1/06* (2013.01);
(Continued)

(58) Field of Classification Search
CPC ............ A61M 27/002; A61M 2207/00; A61M 2207/10; A61M 2210/125;
(Continued)

(56) References Cited

U.S. PATENT DOCUMENTS

2002/0198561 A1* 12/2002 Amplatz .......... A61B 17/12109
606/200
2005/0165344 A1* 7/2005 Dobak .................. A61F 2/2476
604/8
(Continued)

FOREIGN PATENT DOCUMENTS

CN 101642395 A 2/2010
CN 205849480 U 1/2017
(Continued)

OTHER PUBLICATIONS

International Search Report of PCT Application No. PCT/CN2019/105369, mailed on Jun. 22, 2020.

*Primary Examiner* — Jing Rui Ou
(74) *Attorney, Agent, or Firm* — Junhe Law Office P.C.; Zhaohui Wang

(57) ABSTRACT

An atrial shunt regulation device, a braid tool and a braid method thereof. The left disk (1) and the right disk (2) of the atrial shunt regulation device are connected via the intermediate portion (3) as a single piece, and the left disk (1), the intermediate portion (3) and the right disk (2) are braided by a single braid wire (10). The ends of the braid wires are secured by one nut in the single-braid method, which reduces the number and size of the nuts and easily forms a cortical layer. The braid tool for braiding an atrial shunt regulation device comprises a cylinder braid body mold (20), the cylindrical braid body mold (20) includes positioning pins (21) that are evenly connected to an outer wall of the braid body mold. The braid method of the atrial shunt regulation device comprises braiding, thermoforming, braid-
(Continued)

ing a binding-off wire, securing ends of wires by a nut, and thermoforming again. The braid method is easy, the process is easy, and the device can be made manually in small batches to reduce costs.

14 Claims, 7 Drawing Sheets

(51) Int. Cl.
    *A61M 27/00*          (2006.01)
    *D04C 1/06*           (2006.01)

(52) U.S. Cl.
    CPC . *A61B 2017/00526* (2013.01); *A61B 17/0057* (2013.01); *A61B 2017/00592* (2013.01); *A61B 2017/00606* (2013.01); *A61M 2207/00* (2013.01); *A61M 2207/10* (2013.01); *A61M 2210/125* (2013.01); *D10B 2101/20* (2013.01); *D10B 2403/0333* (2013.01); *D10B 2509/00* (2013.01); *D10B 2509/06* (2013.01)

(58) Field of Classification Search
    CPC ........... A61B 2017/00526; A61B 2017/00592; A61B 2017/00606; A61B 17/0057; D03D 1/00; D04C 1/06; D10B 2101/20; D10B 2403/0333; D10B 2509/00; D10B 2509/06
    See application file for complete search history.

(56)         References Cited

U.S. PATENT DOCUMENTS

| | | | |
|---|---|---|---|
| 2006/0136043 A1 | 6/2006 | Cully et al. | |
| 2006/0224183 A1* | 10/2006 | Freudenthal | A61B 17/12031 |
| | | | 606/213 |
| 2009/0198315 A1* | 8/2009 | Boudjemline | D04C 3/48 |
| | | | 623/1.2 |
| 2017/0113026 A1* | 4/2017 | Finch | A61B 17/11 |

FOREIGN PATENT DOCUMENTS

| CN | 106714698 A | 5/2017 |
|---|---|---|
| CN | 109259894 A | 1/2019 |
| CN | 109350139 A | 2/2019 |
| CN | 106714698 B | 11/2020 |

* cited by examiner

1

ATRIAL SHUNT DECOMPRESSION DEVICE, WEAVING DEVICE AND WEAVING METHOD THEREOF

TECHNICAL FIELD

The present application relates to the structure design technical field of an atrial shunt for interventional surgery cardiac treatment, more particularly, relates to an atrial shunt regulation device, a braid tool and a braid method thereof.

BACKGROUND

Heart failure is a common and potentially fatal disease that attacks humans. Despite the patients are maximally treated, poor clinical outcomes often lead to illness, morbidity, and/or death. In particular, "diastolic heart failure" refers to a clinical syndrome of heart failure that occurs in the absence of significant valvular disease with a compensatory left ventricular systolic function (ejection fraction). The characteristics of this disease are left ventricular stiffness with decreased compliance and impaired function relaxation, resulting in increased end-diastolic pressure. About one-third of heart failure patients have diastolic heart failure, and there are few treatments that proven to be effective. Symptoms of diastolic heart failure are, to a great extent, resulted from elevated left atrial pressure. Elevated left atrial pressure (LAP) occurs in several abnormal heart conditions, including heart failure (HF). Besides diastolic heart failure, several other diseases (left ventricular systolic dysfunction and heart valve disease) can cause elevated left atrial pressure. Both heart failure with preserved ejection fraction (HFpEF) and heart failure with reduced ejection fraction (HFrEF) exhibit elevated LAP. It is hypothesized that HF in these two subgroups could benefit from a reduction in LAP, which in turn reduces systolic preload on the left ventricle, and left ventricular end-diastolic pressure (LVEDP). It also reduces pressure on the pulmonary circulation, thereby reducing the risk of suffering pulmonary edema, and improving breathing, and patient comfort.

The prior art disclosed a shut device that is braided by multiple bard wires, and is delivered to the atrial septum of the patient's heart through an interventional device. However, the shunt device in the prior art is all braided by multiple braid wires and secured by multiple nuts. If there are too many braid wires, a large nut is required for fixation, which makes it difficult to form a cortical layer on the surface of the nut, and the adaptability to the human is seriously reduced. The fixation of the nut for multiple braid wires affects the balance and effect of the shunt device.

SUMMARY

In light of above, the main purpose of the present disclosure is to provide an atrial shunt regulation device, a braid tool, and a braid method by means of braiding with a single wire, which realizes the fixation of the all wire ends with one nut, reduces the number and the size of the nuts, thereby forming the cortical layers easily.

The technical solution of the present application is realized as follows:

An atrial shunt regulation device comprises a left disk, a right disk, and an intermediate portion, wherein the left disk and the right disk are connected via the intermediate portion as a single piece; and the left disk, the intermediate portion and the right disk are braided by a single braid wire.

In a preferred embodiment, the braid wire is interweaved to form warp segments and weft segments, and the braid wire passes through the intermediate portion for a plurality of times, and adjacent warp segments and/or adjacent weft segments converge at the intermediate portion, respectively.

In a preferred embodiment, each set of 2-6 successive adjacent warp segments and/or each set of 2-6 successive adjacent weft segments converge at the intermediate portion, respectively.

In a preferred embodiment, each set of 3 successive adjacent warp segments and/or each set of 3 successive adjacent weft segments converge at the intermediate portion, respectively.

In a preferred embodiment, for each set of 3 adjacent warp segments or weft segments, two outer segments of braid wire bend toward a central segment of braid wire, the two outer segments of braid wire extend along the direction of the central segment, and the two outer segments separates at the other end of the central segment for further braiding.

In a preferred embodiment, the segments that converge in a warp and/or weft direction are spirally wrapped for fixation through an end of the braid wire.

In a preferred embodiment, spirally wrapping for fixation is carried out at an intersection of the warp or weft converged braid wire via an end of the braid wire, and an end of the spirally wrapped braid wire converge along the segments in the warp or weft direction between two intersections of segments converged in the same warp or weft direction.

In a preferred embodiment, the device further comprises a binding-off wire for binding off and supporting bending location of the braid wire at an end of the left disk, wherein the binding-off wire extends obliquely to a disk surface of the right disk and is secured to the surface of the right disk by a nut.

In a preferred embodiment, the binding-off wire is wrapped around the bending location of the braid wire in an "S" shape.

In a preferred embodiment, a hole diameter of the binding-off wire at the bending location of the braid wire after being bound off is larger than a diameter of an inner hole of the intermediate portion.

In a preferred embodiment, the binding-off wire extends obliquely to the intermediate portion, is wrapped around transversely at the intermediate portion for 1-8 turns, extends obliquely to the surface of the right disk and is secured to the disk surface of the right disk by the nut.

In a preferred embodiment, the binding-off wire is wrapped in an "S" shape at the intermediate portion between the intersections that are formed from the warp segments that converge to each other and the weft segments that converge to each other.

In a preferred embodiment, an inner hole of the intermediate portion has the same diameter at its upper end, center, and lower end.

In a preferred embodiment, the nut is disposed on one side of the surface of the right disk.

In a preferred embodiment, the nut has a nut hole extending in a direction parallel to the surface of the right disk.

In a preferred embodiment, the binding-off wire has a structure of flat wire at the intermediate portion.

A braid tool for braiding an atrial shunt regulation device, the tool comprises a cylindrical braid body mold, the cylindrical braid body mold includes positioning pins that are evenly connected to an outer wall of the braid body mold so that the braid wire is limitedly wrapped around the outer wall of the braid body mold by the positioning pins.

In a preferred embodiment, the positioning pins include upper bending positioning pins, upper intermediate portion positioning pins, lower intermediate portion positioning pins, and lower bending positioning pins, the upper bending positioning pins and the lower bending positioning pins are disposed on upper and lower sides of the braid body mold, respectively; the upper intermediate portion positioning pins and the lower intermediate portion positioning pins are disposed between the upper bending positioning pins and the lower bending positioning pins.

In a preferred embodiment, an amount of the upper bending positioning pins is the same as an amount of the lower bending positioning pins; an amount of upper intermediate portion positioning pins is the same as a number of the lower intermediate portion positioning pins.

In a preferred embodiment, the planes of the upper bending positioning pins, the upper intermediate portion positioning pins, the lower intermediate portion positioning pins, and the lower bending positioning pins are respectively parallel to each other.

In a preferred embodiment, a distance between the upper bending positioning pins and the upper intermediate portion positioning pins is the same as a distance between the lower bending positioning pins and the intermediate portion positioning pins.

In a preferred embodiment, the amount of the upper bending positioning pins and the amount of the lower bending positioning pins are both 12.

In a preferred embodiment, each of the lower bending positioning pins is on a mid-vertical plane for a connecting line of two adjacent upper bending positioning pins, or each of the lower bending positioning pins is directly beneath one of the upper bending positioning pins.

In a preferred embodiment, the braid body mold includes threading grooves along a vertical direction of the outer wall.

In a preferred embodiment, all the positioning pins are connected to the threading grooves.

A method for braiding an atrial shunt regulation device, the method comprises:

S1, selecting any one of lower bending positioning pins as a starting positioning pin, and obliquely wrapping a braid wire around an outer wall of a braid body mold for a turn from the starting positioning pin to an upper bending positioning pin that positioned directly above the starting positioning pin.

S2, wrapping the braid wire obliquely downward for a turn from the upper bending positioning pin to the lower bending positioning pin that is adjacent to the start positioning pin; wrapping the braid wire obliquely upward for a turn from the adjacent bending positioning pin to an adjacent upper bending positioning pin; and wrapping the braid wire obliquely downward for a turn from the adjacent upper bending positioning pin to a next adjacent lower bending positioning pin;

S3, repeating S2 until the density of the entire braid mesh reaches the set density to form a braid body.

S4, removing all the positioning pins on the braid body mold and disengaging a braid body mold from an inner cavity of the braid body.

S5, thermoforming the braid body for a first time.

S6, setting binding-off wire at the bending location of braid wire formed by the upper bending positioning pins, and wrapping in a direction of "S" shape at the bending location formed by each upper bending positioning pin to tighten and bind off for a predetermined diameter.

4

S7, wrapping the binding-off wire transversely for 1-8 turns when the binding-off wire extends obliquely to the upper end, center, and lower end of the intermediate portion; wrapping in a direction of "S" shape at each intersection of braid wire to bind off for a predetermined diameter;

S8, setting the binding-off wire at the bending location of the braid wire formed by the lower bending positioning pins, and wrapping in a direction of "S" shape at each lower bending positioning pin to bind off for a predetermined diameter.

S9, fixing ends of the braid wire by a nut under the bending positioning pins.

S10, placing the braid body, after being bound off by the binding-off wire, in a fixed mold to thermoform for a second time.

In a preferred embodiment, two ends of the binding-off wire are secured by the nut in step S6.

In a preferred embodiment, wherein the binding-off wire is folded in half and the binding-off wire is, at its folded location of the binding-off wire, disposed onto the bending location of the upper bending positioning pins; the two ends of the binding-off wire respectively pass in an "S"-shape through the bending location of the braid wire formed by all the upper bending positioning pins.

In a preferred embodiment, in step S2, the braid wire passes through between the two adjacent upper intermediate portion positioning pins and the two adjacent lower intermediate portion positioning pins when the braid wire is wrapped upward from the lower bending positioning pins to the upper bending positioning pins.

In a preferred embodiment, during the oblique wrapping, the successive adjacent 2-6 wire segments along the same direction passes through the same pair of upper intermediate portion positioning pin and lower intermediate portion positioning pin.

In a preferred embodiment, during the oblique wrapping, each wire segment extending in a direction warps inside and outside over 2 to 6 wire segments extending in another direction, between the upper bending positioning pin and the upper intermediate portion positioning pin, and between the lower bending positioning pin and the lower intermediate portion positioning pin, respectively.

In a preferred embodiment, during the oblique wrapping, the successive adjacent 3 wire segments along the same direction passes through the same pair of upper intermediate portion positioning pin and lower intermediate portion positioning pin.

In a preferred embodiment, each wire segment extending in a direction warps inside and outside over 3 wire segments extending in another direction the upper bending positioning pin and the upper intermediate portion positioning pin and between the lower bending positioning pin and the lower intermediate portion positioning pin, respectively.

The left disk and the right disk of the atrial shunt regulation device are connected via the intermediate portion as a single piece, and the left disk, the intermediate portion and the right disk are braided by a single braid wire. All ends of the braid wires are secured by one nut in the single-braid method, which reduces the number and size of the nuts and easily forms a cortical layer. It solves the problem that the size of nuts in the multi-wire method is large, it is difficult to form a cortical layer, and nuts are secured on both the left disk and right disk, resulting in an unbalanced structure and uneven force.

The braid tool for braiding an atrial shunt regulation device comprises a cylinder braid body mold, the cylindrical braid body mold includes positioning pins that are evenly connected to an outer wall of the braid body mold so that the braid wire is limitedly wrapped around the outer wall of the braid body mold by the positioning pins. It can realize a single-wire braid method that ensures the forming of a shunt regulation device with a single-wire.

The braid method of the atrial shunt regulation device comprises braiding, thermoforming, braiding a binding-off wire, securing ends of wires by a nut and thermoforming again. The braid method is easy, the process is easy, and the device can be made manually in small batches to reduce costs.

NUMERICAL ILLUSTRATION OF MAIN COMPONENTS

1—left disk; 2—right disk; 3—intermediate portion; 4—nut; 10—braid wire; 11—warp segment; 12—weft segment; 13—intersection; 20—braid body mold; 21—positioning pin; 211 upper bending positioning pin; 212—upper intermediate portion positioning pin; 213—lower intermediate portion positioning pin; and 214—lower bending positioning pin.

DETAILED DESCRIPTION

An atrial shunt regulation device, a braid tool, and a braid method of the present disclosure will be described in further detail below in connection with the drawings and the embodiments of the present disclosure.

Figure 1:
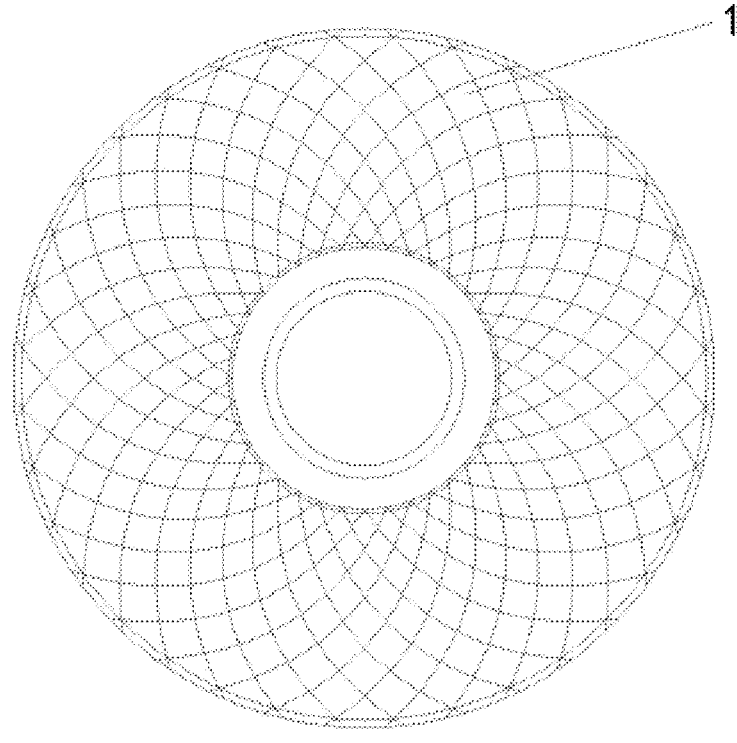
FIG. 1 is a top view of an atrial shunt depressurization device according to one embodiment of the present disclosure.
Figure 2:
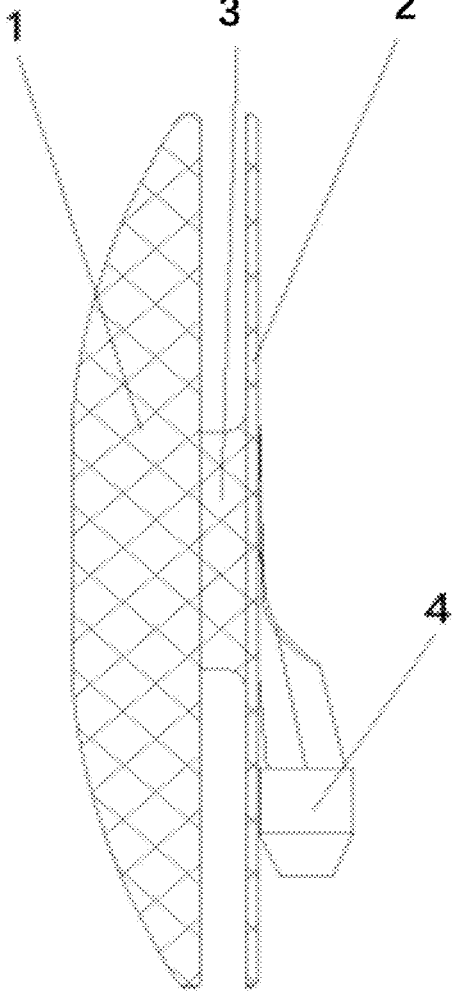
FIG. 2 is a side view of the atrial shunt regulation device according to one embodiment of the present disclosure.
Figure 3:
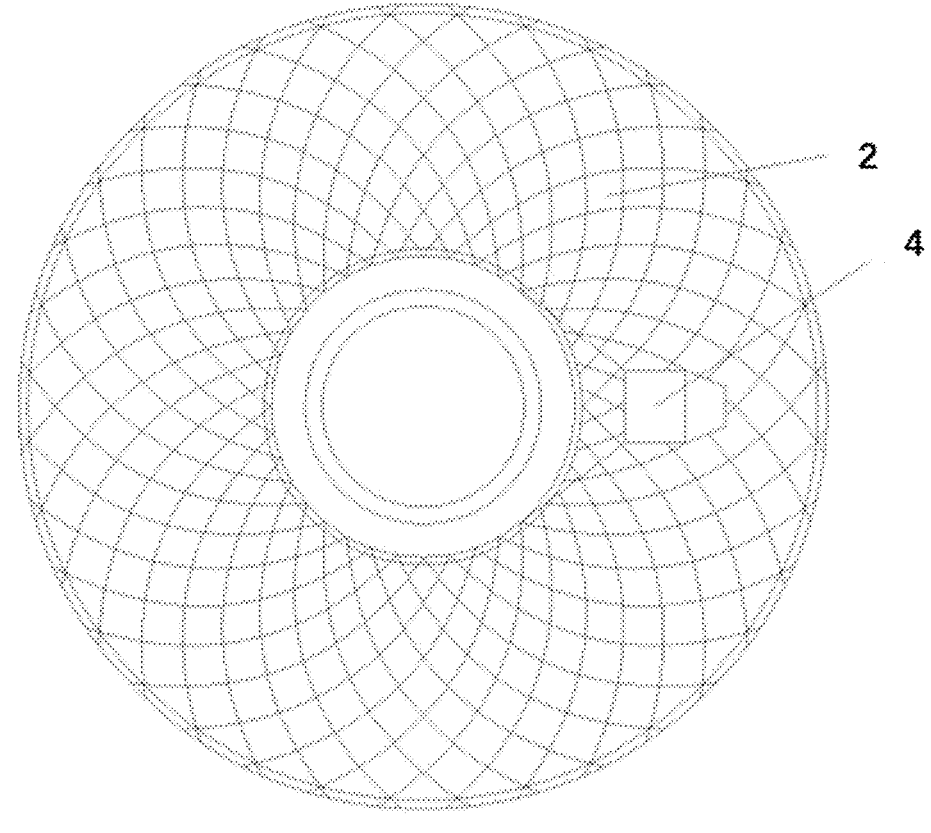
FIG. 3 is a bottom view of the atrial shunt regulation device according to one embodiment of the present disclosure.
Figure 4:
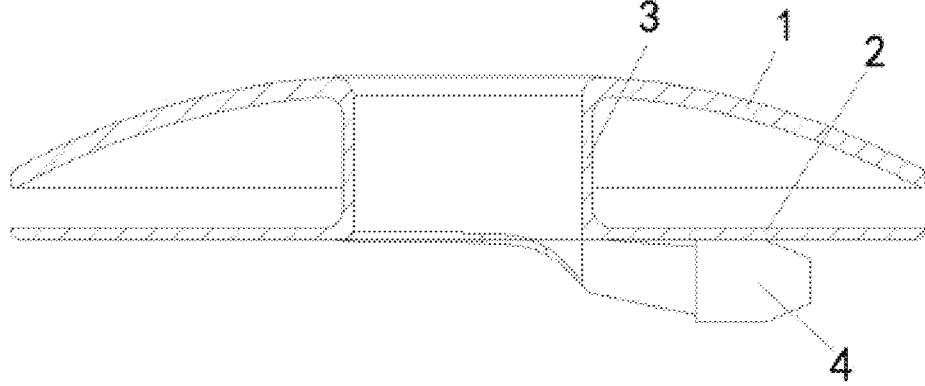
FIG. 4 is a cross-sectional view of the atrial shunt regulation device according to one embodiment of the present disclosure.
Figure 5:
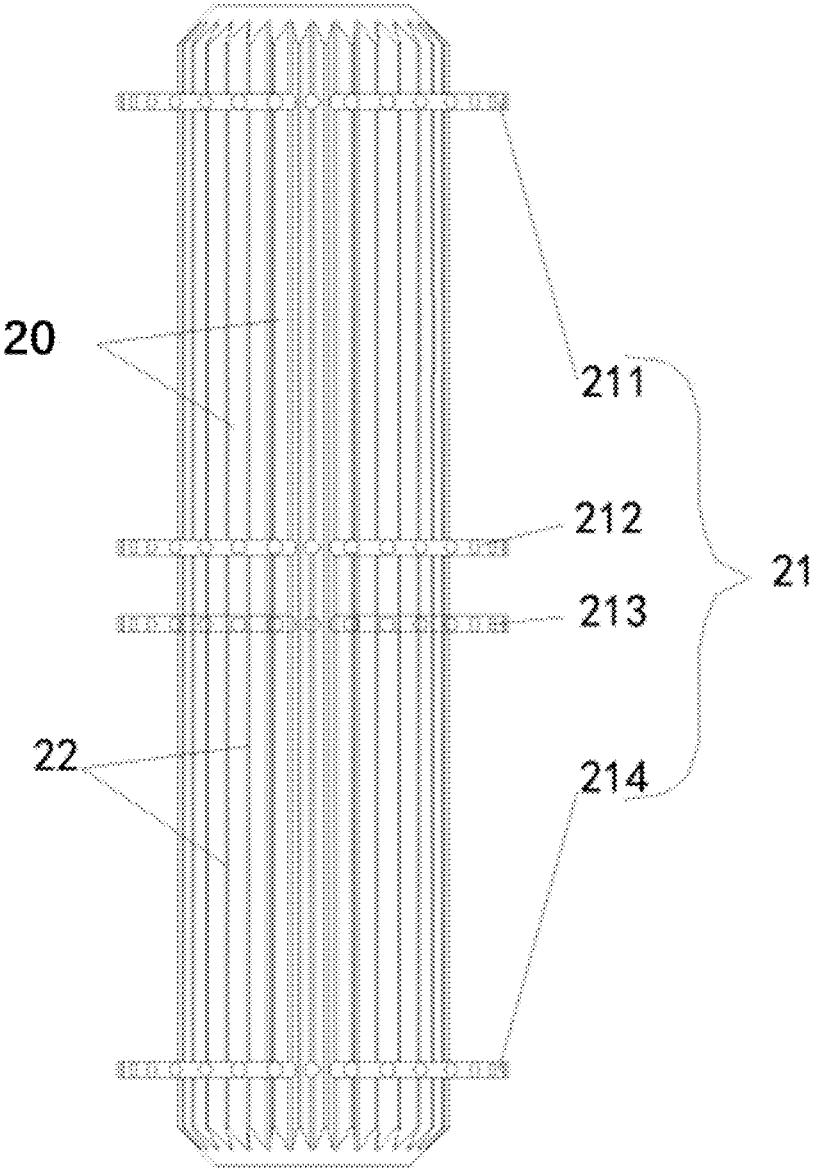
FIG. 5 is a front view of a braid tool for braiding an atrial shunt regulation device according to an embodiment of the present disclosure.
Figure 6:
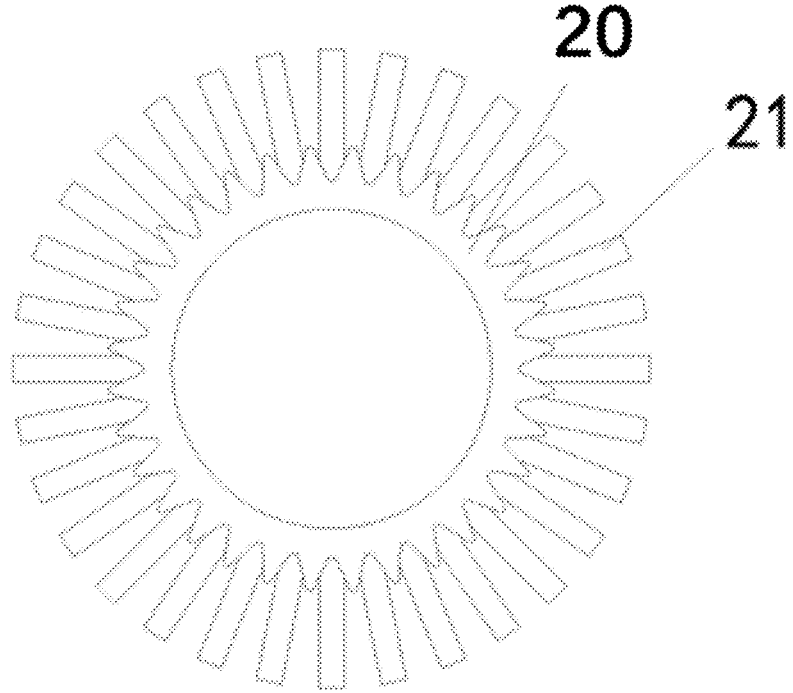
FIG. 6 is a top view of braid tool for braiding an atrial shunt regulation device according to one embodiment of the present disclosure.
Figure 7:
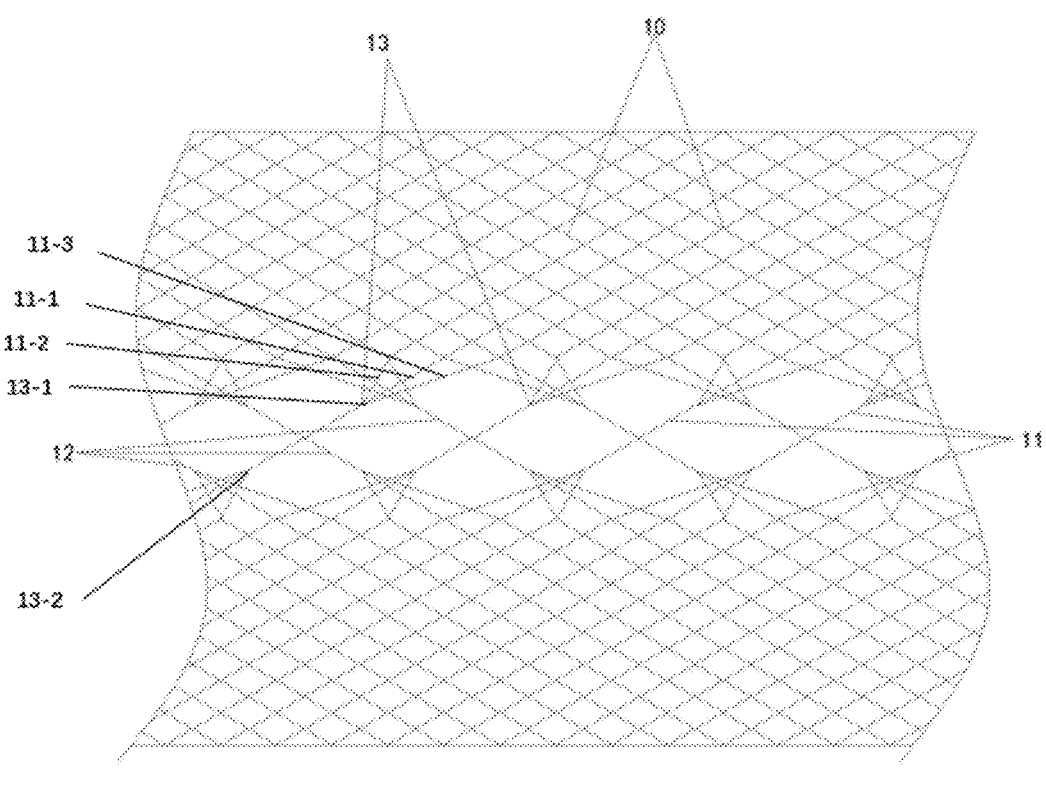
FIG. 7 is a partially enlarged schematic view of a braid body made by the braid method of the atrial shunt regulation device.

As shown in FIGS. 1-7, an atrial shunt regulation device includes a left disk 1 and a right disk 2 that are respectively disposed on a septum between the left atrium and the right atrium, and an intermediate portion 3 connecting the left disk 1 and the right disk 2 as a single piece.

To reduce the size of the fasteners (rivets, nuts, etc.) for fixing the ends of the braid wire, the left disk 1, the intermediate portion 3, and the right disk 2 are braided by a single braid wire 10. The braid wire 10 is braided into a structure as a single piece, and all segments of the braid wire 10 are connected with each other to ensure the strength of the regulation device. The size of two fasteners (rivets, nuts, etc.) for the braid wire 10 in single-wire braid method is much smaller than that in the multi-wire (more than one)

braid method in the prior art (the size of fasteners in the regulation device of the present application is ⅕-½ of the size of fasteners in the prior art), which can greatly reduce the size of an interventional device. Furthermore, the scope of interventional surgery treatment can be expanded. That is, patients such as children or the elderly with thin blood vessels can also be treated. In the prior art, a regulation device is braided by multi-wire instead of a single wire. Especially in the prior art of braid method, braid wires can only be braided obliquely from one direction to another, and only multiple wires can meet the requirement of braid density. For those skilled in the art, there is a technical prejudice for the braid method of a single wire, and it is agreed that the braid method of a single wire cannot be adopted, so that the braid method of a single wire has not been studied yet. Considering that multi-wire braid can speed up the processing procedure especially in the mechanized production, there is a technical prejudice by a person skilled in the art for the braid method of a single wire.

In addition, the smaller the size of the fastener, the better fitting the fastener is on the surface of the right disk, which facilitates endothelialization and ensures adaptability with the fluid in the body.

By increasing the mesh size of the intermediate portion 3 and reducing the density of the mesh on condition that the height of the intermediate portion is not reduced, the thickness of the cortical layer formed at the intermediate portion is reduced. By avoiding the cortical layer being too thick (which reduces the guiding effect of the regulation device) at the intermediate portion 3, the cortical layer can be avoided to block the inner hole of the intermediate portion 3 during the long-term use of the regulation device. The braid wire 10 is interweaved to form warp segments 11 and weft segments 12, and the braid wire 10 passes through the intermediate portion 3 for a plurality of times, and the adjacent warp segments 11 and/or adjacent weft segments 12 converge at the intermediate portion 3 respectively (the adjacent warp segments 11 at the intermediate portion 3 converge; and/or the adjacent weft segments 12 at the intermediate portion 3 converge, the weft segments 11 and the weft segments 12 are braided instead of other connection relationship). The converged segments can be some converged warp segments and/or some converged weft segments, not all segments must be converged, and of course, all segments could be converged. The total strength of the converged segments does not decrease, and the strength of the single-strand braid wire (the segments are converged as one strand) also increases, which improves the strength stability of the entire regulation device.

Preferably, for the braid wire 10 at the intermediate portion 3, each adjacent 2-6 successive warp segments 11 and/or each adjacent 2-6 successive weft segments 12 converge at the intermediate portion 3. That is, the first segment to second or sixth segment converge together. The number of segments for each strand may not be the same, as long as the balance and stability of the structure of the intermediate portion 3 can be ensured.

Preferably, for the braid wire 10 at the intermediate portion 3, each adjacent 3 successive warp segments 11 and/or each adjacent 3 successive weft segments 12 converge at the intermediate portion 3. That is: preferably, the number of warp segments 11 and weft segments 12 are both multiples of the number three, which ensures that each strand has the same number of segments, and all the segments are braided within the respective strand and realize the balance of the intermediate portion 3.

Specifically, the structure of the 3 braid segments is as follows: for each set of 3 adjacent warp segments 11 or 3 adjacent weft segments 12, two outer segments 11-2 and 11-3 of braid wire 10 bend toward a central segment 11-1 of braid wire 10, the two outer segments 11-2 and 11-3 of braid wire 10 extend along the direction of the central segment 11-1, and the two outer segments 11-2 and 11-3 separates at the other end of the central segment 11-1 for further braiding. That is: the segments converge to form a strand-shaped braid wire, and at the two end of the strand-shaped braid wire, the three segments are separated into a left segment, a middle segment, and a right segment. The left segment and the right segment respectively bend towards the middle segment at the two ends of the strand of segments, thus forming the strand-shaped braid wire.

To ensure the binding force between the plurality of segments in each strand of segments (for example, when the three segments converge together, if the converge force among them is not enough, it is easy for them to separate, so that the effect of converging three segments together would disappear). The segments that converge in the warp direction and/or the weft direction are fixed by being spirally wrapped with an end of braid wire 10. Only two ends of the strand of segments are fixed by being spirally wrapped, so as to ensure the strength of the strand of segments, while avoiding the excessive compression size of the intermediate portion, which may affect the intervention of the device.

Certainly, in another embodiment, to ensure the converge and binding force of the strand of wire segments, spirally wrapping for fixation is carried out at an intersection 13 of the warp or weft converged braid wire 10 via an end of the braid wire 10. The end of the braid wire 10 for spirally wrapping converge along with the segments in the warp or weft direction between two intersections 13-1 and 13-2 of segments converged in the same warp or weft direction.

To ensure the fixation and support at the bending location of the braid wire (that is the upper end of the braid body), the regulation device further includes: a binding-off wire for binding off and supporting bending location of the braid wire at an end of the left disk 1. The braid wire at the bending location is connected together by the binding-off wire to ensure the strength of fixation. The binding-off wire extends obliquely to a surface of the right disk 2 and is secured to the surface of the right disk 2 by a nut 4. As a result, the overall connection strength of the binding-off wire is ensured, other fasteners are not required, and the size of the regulation device is increased. The left disk 1 has no rivets, thereby avoiding stress eccentricity at the end of the left disk 1, and increasing the symmetry of the surface of the disk and the stability of intermediate portion.

To ensure the strength of fixation for the braid wire, the binding-off wire wraps along an "S" shape at the bending location of the braid wire 10, so that the interaction between the braid wire and the binding-off wire not only realizes the support and fixation of the braid wire, but also avoids the slippage of the binding-off wire, which further ensures the strength of fixation for the braid wire.

Since there are many bending structures at the bending location of the braid wire 10, it is easy to form a cortical layer at the bending location. To cover the bending location, the cortical layer is usually relatively thick. To avoid limiting the hole diameter of the intermediate portion at the bending location of braid wire 10 (thereby limiting the depressurization flow of the shunt regulation device), the hole diameter of the binding-off wire at the bending location of the braid wire 10 after being bound off is larger than a diameter of an inner hole of the intermediate portion 3 to ensure that the size of the entire shunt regulation device is limited by the hole diameter of the intermediate portion.

To further ensure the support strength of the intermediate portion 3 and the strength of the entire regulation device, the binding-off wire extends obliquely to the intermediate portion 3 and wraps transversely around the intermediate portion 3 for 1-8 turns, and an end of the binding-off wire extends obliquely to disk surface of the right disk 2 and is secured to the surface of the right disk 2 by the nut 4.

To ensure the strength of fixed connection of the binding-off wire at the intermediate portion 3, the binding-off wire wraps in an "S" shape at the intermediate portion 3 between the intersections 13-1 and 13-2 of segments that are formed by the converged warp segments 11 and the converged weft segments 12. As a result, the binding-off wire is secured by the braid wire 10, so that the location of the binding-off wire is unaltered to ensure the supporting of the intermediate portion 3.

Preferably, an inner hole of the intermediate portion 3 has the same diameter at its upper end, center portion and lower end, to ensure the effect of shunt regulation by the inner hole of the intermediate portion 3.

Preferably, the nut 4 is disposed on one side of an upper surface of the right disk 2. In other words, the nut is offset so that the nut 4 is positioned more adjacent to the atrial septum, which facilitates endothelialization to cover the nut 4.

To facilitate withdrawal or replacement of the regulation device, the nut 4 has a nut hole extending in a direction parallel to the surface of the right disk 2. In the process of withdrawal or replacement, the interventional device may include a wire trap inserted into the regulation device. The wire trap may be intervened to the location of the regulation device and capture the transverse nut, so that the entire regulation device can be pulled into an interventional tube, thereby realizing the withdrawal of the entire regulation device and reducing the surgical risk.

To further improve the support of the binding-off wire at the intermediate portion 3, preferably, the binding-off wire has a structure of flat wire at the intermediate portion 3. Preferably, the flat wire is not formed by directly being pressed, and the whole binding-off wire is formed as a single piece. The cross-sectional area at the flat wire is larger than the cross-sectional area at other positions of the binding-off wire.

A braid tool for braiding an atrial shunt regulation device is disclosed in the present disclosure. The braid tool includes a cylinder braid body mold 20 for supporting and securing a braid wire. The cylinder braid body mold 20 includes positioning pins 21 that are evenly connected to an outer wall of the braid body mold 20, so that the braid wire 10 wraps around the outer wall of the braid body mold 20 by the limitation of the positioning pins 21. The positioning pins 21 can change the braid direction of the braid wire, thereby defining the braid structure of the braid wire and forming the braid body.

The positioning pins 21 include upper bending position pins 211 for defining a bending location of the braid wire 10 from extending upward to downward, upper intermediate portion positioning pins 212 and lower intermediate portion positioning pins 213 for adjusting a braid direction of the braid wire 10, and lower bending positioning pins 214 for limiting a bending location of the braid wire from extending downward to upward. The upper bending positioning pins 211 and the lower bending positioning pins 214 are disposed on upper and lower sides of the braid body mold 20, and do not completely reach to the ends. A certain space that is reserved at the upper and lower ends can facilitate the subsequent braiding. Certainly, in order to realize the limitation of the direction of the braid wire 10, the upper intermediate portion positioning pins 212 and the lower intermediate portion positioning pins 213 are disposed between the upper bending positioning pins 211 and the lower positioning pins 214.

To ensure that each positioning pin can be used to avoid redundancy of positioning pins (the redundant positioning pins 21 may interfere with braiding of the braid body), the amount of the upper bending positioning pins 211 is the same as the amount of the lower bending positioning pins 214; the amount of upper intermediate portion positioning pins 212 is the same the lower intermediate portion positioning pins 213.

In addition, to ensure the braiding of braid body between the positioning pins of respective locations, the planes of the upper bending positioning pins 211, the upper intermediate portion positioning pins 212, the lower intermediate portion positioning pins 213, and the lower bending positioning pins 214 may be respectively parallel to each other.

To ensure that the left disk 1 and the right disk 2 are symmetrical to each other, the distance between the upper bending positioning pins 211 and the upper intermediate portion positioning pins 212 is the same as the distance between the lower bending positioning pins 213 and the intermediate portion positioning pins 214.

Preferably, it is most reasonable for the structure of an atrial regulation device in practice to have twelve upper bending positioning pins 211 and twelve lower bending positioning pins 212, so as to realize a better shunt effect, while avoiding the excessive density of the braid wire which affects the intervention process.

To ensure that the whole braided regulation device is more reasonable in structure, especially all the upward braid wire segments and the downward braid wire segments are inclined at the same angle (that is, the warp segments and the weft segments have a same angle with respect to a central axis of the regulation device respectively), each of the lower bending positioning pins 214 is positioned on a mid-vertical plane of two adjacent upper bending positioning pins 211, or each of the lower bending positioning pins 214 is positioned directly beneath one of the upper bending positioning pins 211.

In order to facilitate the traverse of the braid wire 10 and ensure the strength of the braiding, the braid body mold 20 includes braiding grooves 22 along a vertical direction of cylinder wall. During the braiding of the braid wire 10, when an end of a wire is required to insert though the beneath of the braid wire 10, the end of the wire can pass through the braiding grooves 22 for the facilitation of braiding.

To ensure the fixation strength of the positioning pins 21 and to facilitate the braiding process, all the positioning pins 21 are connected within the threading grooves 22. Preferably, the positioning pins 21 each has a threaded end, which is connected with a corresponding threaded hole at the bottom of the threading grooves 22.

A method for braiding an atrial shunt regulation device is provided, and the method includes:

S1, selecting any one of the lower bending positioning pins 214 as a starting positioning pin (just for the clarity of the technical solution and has a clear naming), and obliquely wrapping the braid wire 10 around an outer wall of the braid body mold 20 for a turn from the starting positioning pin to an upper bending positioning pin 211 that is right above the starting positioning pin (in order to observe the braiding position accurately, the upper bending positioning pin positioned right above is selected, and a upper bending positioning pin 211 in a different position can be selected during the specific braiding process when automatic braiding is realized in the later stage). S2, wrapping the braid wire obliquely downward for a turn from the side of the upper bending positioning pin 211 to the lower bending positioning pin 214 that is adjacent to the start positioning pin (for example, obliquely from the bottom up, the adjacent lower bending positioning pin 214 can be the next one to the left of the starting positioning pin); wrapping the braid wire obliquely upward for a turn from the adjacent bending positioning pin 214 to an adjacent upper bending positioning pin 211 (similar to step S1); and wrapping the braid wire obliquely downward for a turn from the side of the adjacent upper bending positioning pin 211 to a next adjacent lower bending positioning pin 214. S3, repeating step S2 until the density of the entire weave mesh reaches a set density to form a braid body (it can be understand that the braid wire is evenly braided on the outer wall of the braid body mold 20) S4, removing all the positioning pins 21 on the braid body mold 20 (the positioning pins 21 are detachably connected so that the braid body can be easily separated from the braid body mold 20), and disengaging the cylinder braid body mold 20 from an inner cavity of the braid body. S5, thermoforming the cylindrical braid body for the first time (ensure that the entire braid body maintains a certain structural shape). S6, setting a binding-off wire at the bending location of braid wire at the upper bending positioning pins 211, and wrapping in a direction of "S" shape at the end of each upper bending positioning pin 211 to tighten and bind off for a predetermined diameter. S7, wrapping the binding-off wire transversely for 1-8 turns when the binding-off wire extends obliquely to the upper portion, the central portion, and the lower portion of the intermediate portion, and wrapping in a direction of "S" shape at each intersection 13 of braid wire 10 to binding off for a predetermined diameter. S8, setting the binding-off wire at the bending location of the lower bending positioning pins 214, and wrapping in a direction of "S" shape at each lower bending positioning pin 214 to bind off for a predetermined diameter. S9, fixing the end of braid wire 10 by a nut 4 beneath the bending positioning pins 214. S10, placing the braid body after being bound off by the binding-off wire in a fixed mold to thermoform for the second time, so as to obtain a desired product as shown in FIGS. 1-4.

Preferably, two ends of the binding-off wire are secured by nut 4 in step S6.

The binding-off wire is folded in half for use (further ensure that the positioning and fixation effect at the bending location of the upper bending positioning pins 211), and the binding-off wire is disposed onto the bending location of the upper bending positioning pins 211 at the folded location of the binding-off wire; the two ends of the binding-off wire respectively pass in an "S"-shape through the bending location of all the upper bending positioning pins 211.

Preferably, in step S2, when the braid wire 10 wraps upward from the lower bending positioning pin 214 to the upper bending positioning pin 211, the braid wire 10 passes through between the two adjacent upper intermediate portion positioning pin 212 and lower intermediate portion positioning pin 213; the braid wire 10 passing through between the two adjacent upper intermediate portion positioning pin 212 and lower intermediate portion positioning pin 213 when the braid wire 10 wraps upward from the lower bending positioning pin 214 to the upper bending positioning pin 211 can ensure the fixation of the braid wire.

Preferably, during the oblique wrapping, the successive adjacent 2-6 wire segments along the same direction passes through the same pair of upper intermediate portion positioning pin 212 and lower intermediate portion positioning pin 213.

Preferably, during the oblique wrapping, each wire segment 10 extending in a direction warps inside and outside over 2 to 6 wire segments 10 extending in another direction, between the upper bending positioning pin 211 and the upper intermediate portion positioning pin 212, and between the lower bending positioning pin 214 and the lower intermediate portion positioning pin 213, respectively.

Preferably, during the oblique wrapping, the successive adjacent 3 wire segments along the same direction passes through the same pair of upper intermediate portion positioning pin 212 and lower intermediate portion positioning pin 213.

Preferably, during the oblique wrapping, each wire segment 10 extending in a direction warps inside and outside over 3 wire segments 10 extending in another direction, between the upper bending positioning pin 211 and the upper intermediate portion positioning pin 212 and between the lower bending positioning pin 214 and the lower intermediate portion positioning pin 213, respectively.

The above descriptions are only preferred embodiments of the present invention and are not intended to limit the protection scope of the present invention.

What is claimed is:

1. An atrial shunt regulation device comprising: a left disk (1), a right disk (2), and an intermediate portion (3), wherein the left disk (1) and the right disk (2) are connected via the intermediate portion (3) as a single piece; and wherein the left disk (1), the intermediate portion (3) and the right disk (2) are braided by a single braid wire (10);

wherein the braid wire (10) is interweaved to form warp segments (11) and weft segments (12), and the braid wire (10) passes through the intermediate portion (3) for a plurality of times, and wherein adjacent warp segments (11) and/or adjacent weft segments (12) converge at the intermediate portion (3), respectively;

wherein each set of 2-6 adjacent warp segments (11) and/or each set of 2-6 adjacent weft segments (12) converges at the intermediate portion (3), respectively, such that the 2-6 adjacent warp segments (11) in the respective set or the 2-6 adjacent weft segments (12) in the respective set join together at a first intersection (13-1) and separate at a second intersection (13-2).

2. The atrial shunt regulation device according to claim 1, wherein each set of 3 adjacent warp segments (11) and/or each set of 3 adjacent weft segments (12) converges at the intermediate portion (3), respectively.

3. The atrial shunt regulation device according to claim 2, wherein each set of three adjacent warp segments (11) have a central warp segment (11-1) and two outer warp segments (11-2 and 11-3), and wherein the two outer warp segments (11-2 and 11-3) bend toward the central warp segment to join with the central warp segment at the first intersection (13-1), and bend away from the central warp at the second intersection (13-2) to be separated from the central warp segment.

4. The atrial shunt regulation device according to claim 1, wherein the segments that converge in a warp and/or weft direction are spirally wrapped for fixation through an end of the braid wire (10).

5. The atrial shunt regulation device according to claim 1, wherein the segments that converge in the warp and/or weft direction are spirally wrapped for fixation at the intersections (13-1 and 13-2) of the braid wire (10) through an end of the braid wire (10), the end of the spirally wrapped braid wire (10) converges together with the segments that converge in the warp and/or weft direction between the intersections (13-1 and 13-2) of the braid wire (10).

6. The atrial shunt regulation device according to claim 1, wherein the device further comprises:

a binding-off wire for binding off and supporting bending location of the braid wire at an end of the left disk (1), wherein the binding-off wire extends obliquely to a surface of the right disk (2) and is secured to the surface of the right disk (2) by a nut (4).

7. The atrial shunt regulation device according to claim 6, wherein the binding-off wire is wrapped around the bending location of the braid wire (10) in an "S" shape.

8. The atrial shunt regulation device according to claim 6, wherein a diameter of the binding-off wire at the bending location of the braid wire (10) is larger than a diameter of an inner hole of the intermediate portion (3).

9. The atrial shunt regulation device according to claim 6, wherein the binding-off wire extends obliquely to the intermediate portion (3), is wrapped around transversely at the intermediate portion (3) for 1-8 turns, extends obliquely to the surface of the right disk (2) and is secured to the surface of the right disk (2) by the nut (4).

10. The atrial shunt regulation device according to claim 9, wherein the binding-off wire is wrapped in an "S" shape at the intermediate portion (3) between the intersections (13) that are formed from the warp segments (10) that converge to each other and the weft segments that converge to each other.

11. The atrial shunt regulation device according to claim 9, wherein an inner hole of the intermediate portion (3) has the same diameter at its upper end, center, and lower end.

12. The atrial shunt regulation device according to claim 9, wherein the nut (4) is disposed on one side of the surface of the right disk.

13. The atrial shunt regulation device according to claim 12, wherein the nut (4) has a nut hole extending in a direction parallel to the surface of the right disk (2).

14. The atrial shunt regulation device according to claim 6, wherein the binding-off wire has a structure of flat wire at the intermediate portion (3).

* * * * *